United States Patent
Lee et al.

(10) Patent No.: US 7,229,980 B2
(45) Date of Patent: Jun. 12, 2007

(54) PAROXETINE CHOLATE OR CHOLIC ACID DERIVATIVE SALTS, AND COMPOSITION COMPRISING PAROXETINE AND CHOLIC ACID OR DERIVATIVE THEREOF

(75) Inventors: Sang Joon Lee, Kunpo-si (KR); Hee Jong Shin, Bucheon-si (KR); Min Hyo Ki, Cheonan-si (KR); Su Kyoung Lee, Cheonan-si (KR); Bok Young Kim, Cheonan-si (KR); Hong Woo Lee, Ansan-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 339 days.

(21) Appl. No.: 11/048,310

(22) Filed: Jan. 31, 2005

(65) Prior Publication Data

US 2006/0063747 A1    Mar. 23, 2006

(30) Foreign Application Priority Data

Sep. 21, 2004   (KR) ...................... 10-2004-0075458

(51) Int. Cl.
*A61K 31/56*   (2006.01)
*C07D 215/04*  (2006.01)

(52) U.S. Cl. .......................................... 514/171; 540/2
(58) Field of Classification Search ................ 514/171; 540/2

See application file for complete search history.

(56) References Cited

U.S. PATENT DOCUMENTS 4,721,723 A    1/1988   Barnes et al. ................ 514/321

FOREIGN PATENT DOCUMENTS

| WO | WO 95/20964 | 8/1995 |
| WO | WO 99/32484 | 7/1999 |
| WO | WO 99/40084 | 8/1999 |
| WO | WO 99/52901 | 10/1999 |
| WO | WO 99/55699 | 11/1999 |
| WO | WO 00/01692 | 1/2000 |
| WO | WO 00/01694 | 1/2000 |
| WO | WO 03/013470 A1 | 2/2003 |
| WO | WO 03/013529 A1 | 2/2003 |

OTHER PUBLICATIONS

Remeron Sol Tab®— Compliance © 2004 NV Orgamon.
Cholic Acid Product information date needed.

*Primary Examiner*—Barbara P. Badio
(74) *Attorney, Agent, or Firm*—Jones Day

(57) ABSTRACT

Disclosed herein is a paroxetine cholate or cholic acid derivative salt and a composition comprising paroxetine and cholic acid or a derivative thereof. Further disclosed is a pharmaceutical composition comprising the paroxetine salt or the composition. The pharmaceutical composition can be formulated into an oral preparation for swallowing without water as an orally disintegrating tablet for paroxetine.

15 Claims, No Drawings

PAROXETINE CHOLATE OR CHOLIC ACID DERIVATIVE SALTS, AND COMPOSITION COMPRISING PAROXETINE AND CHOLIC ACID OR DERIVATIVE THEREOF

TECHNICAL FIELD

The present invention relates to paroxetine cholate or cholic acid derivative salts, and a composition comprising paroxetine and cholic acid or a derivative thereof.

BACKGROUND ART

Paroxetine has the chemical formula (−)-(3S,4R)-4-(p-fluorophenyl)-3-[(3,4-methylenedioxy)phenoxy]-methyl] piperidine, and is used as a therapeutic agent for the treatment of depression, panic disorder, pre-menstrual dysphoric disorder and social phobia by taking advantage of a typical selective serotonin (5-HT) reuptake inhibitor (SSRI) mechanism.

It is reported that since general anti-depressants, including paroxetine, have poor medication compliance in patients, the development of oral formulations for swallowing without water will improve the medication compliance of patients by decreasing the sensation of medicine administration. According to clinical results of Remeron SolTab (manufactured under the trade name Mirtazapine by Janssen), which is the first developed oral anti-depressant for swallowing without water in the world, continuous treatment of depression without stopping in the initial stage is mentioned as a critical factor in the improvement of symptoms in a depressive patient. A study on patients who had been administered Remeron SolTab reported that the patients preferred SolTab preparations to other conventional pills. This study also reported that the proportion of patients responding the selection of SolTab is six times higher than that responding the selection of other pills. These results reveal that the use of anti-depressants for swallowing without water improves therapeutic compliance in patients and thus better results in the treatment of depression and the prevention of depression recurrence can be expected.

However, paroxetine has a very bitter taste even at low concentrations, whilst it causes irritating pain along with a very bitter taste at high concentrations due to its inherent characteristics. Accordingly, paroxetine is limited in its ability to be developed into solid oral formulations for swallowing without water. Although paroxetine can be coated with or included in materials, such as polymers and cyclodextrins, by common techniques known in the art, the bitter taste of paroxetine is incompletely masked. Particularly, when paroxetine is formulated into a tablet, the shape of the coated or included granule may be partially collapsed to expose the contents to the outside of the granule, which render an uncomfortable sensation in the mouth. In order to wholly or partially block the bitter and irritant taste of paroxetine, the use of excipients in large quantities is necessary. Accordingly, it is substantially impossible to develop an orally disintegrating tablet.

PCT Publication WO 95/020964 discloses a process for formulating a liquid preparation (liquid for medication) by dispersing a water-insoluble ion exchange resin in water and formulating the dispersion with a drug, thereby masking the bitter taste of the drug. However, since the ion exchange resin is insoluble in water, it cannot be uniformly distributed in an aqueous phase and thus the bitter taste of the drug cannot be completely masked.

In efforts for masking the inherent taste of paroxetine with another taste, glycyrrhyzinic acid or glycyrrhyzinate salts are found in PCT Publications WO 03/013470 and WO 03/013529. These publications mention that since glycyrrhyzinate as a main ingredient of liquorice has itself an intense flavor of sweet liquorice, it can contribute to masking the bitter taste of paroxetine. In fact, the abstracts of the publications describe that because of the intensity of liquorice flavor even in a state where glycyrrhyzinate is formulated, further flavorings may be desirable to modify the liquorice taste of the formulation.

A number of studies on salts of paroxetine have been actively undertaken. For example, U.S. Pat. No. 4,721,723 and PCT Publication WO 99/32484 describe paroxetine hydrochloride; PCT Publication WO 99/52901 describes paroxetine maleate; PCT Publication WO 99/55699 describes paroxetine camphorsulfonates; PCT Publication WO 99/55698 describes paroxetine ascorbate; PCT Publication WO 00/01694 describes paroxetine methanesulfonate; PCT Publications WO 03/013470 and WO 03/013529 describe glycyrrhyzinate or glycyrrhyzinate salts; PCT Publication WO 99/40084 describes salts of paroxetine with acids, including sulfuric, tartaric, oxalic, fumaric, propionic, formic, glutamic, succinic, benzoic, citric, nitric, phosphoric, 4-methylbenzenesulfonic, hypophosphorous, lactic, and mandelic acids, without detailed explanations regarding the salts; and PCT Publication WO 00/01692 describes salts of paroxetine with an acid group. However, none of the above patent publications mention an improvement in taste associated with the use of the paroxetine salts.

In addition to these salts of paroxetine, PCT Publication WO 95/20964 claims a liquid oral preparation using a paroxetine-amberlite complex. However, the amberlite resin is not a monomolecular material, but a polymeric material carrying many charges in a single molecule, and is particularly insoluble in water or solvents. The molecular weight of polymers can be expressed only by average molecular weight due to the characteristics of polymers. Accordingly, the binding molar ratio of the amberlite resin to the drug cannot be precisely attained, unlike monomolecular salts, and thus it is difficult to say that the paroxetine-amberlite complex is a salt. In addition, the taste-masking effects of the polymeric resin are due to the dispersion of the water-insoluble resin-drug complex in water. Accordingly, the effects of the complex are distinguished from those of paroxetine salts.

Little has heretofore been reported, suggested, or experimentally proved about the absence of taste and pain of paroxetine, and the greatly improved stability of paroxetine through the formation of paroxetine salts. Particularly, there are no reports about paroxetine cholate and cholic acid derivative salts.

Thus, it is an object of the present invention to provide a paroxetine salt or a paroxetine composition capable of causing changes in the characteristics of paroxetine molecular units to change the taste properties of paroxetine such that the bitter taste of paroxetine, even after it is completely dissolved in water, is removed in the salt or the composition.

It is another object of the present invention to provide a paroxetine oral preparation for swallowing without water, namely an orally disintegrating tablet, comprising the paroxetine salt or the paroxetine composition.

DISCLOSURE OF THE INVENTION

In accordance with one aspect of the present invention, there is provided a paroxetine cholate or cholic acid derivative salt. The paroxetine cholate salt is particularly preferred.

In accordance with another aspect of the present invention, there is provided a composition comprising paroxetine and cholic acid or a derivative thereof.

Cholic acid and its derivatives are represented by Formula 1:

Formula 1

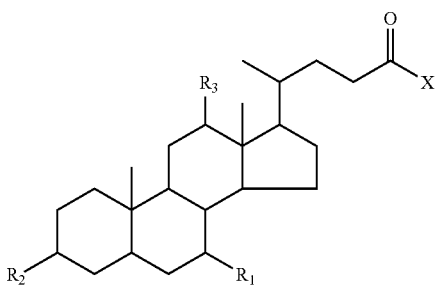

wherein $R_1$, $R_2$, and $R_3$ are independently hydrogen or a hydroxy group; and X is —OH, —ONa, —NH—$(CH_2)_n$—$SO_3H$, —NH—$(CH_2)_n$—$SO_3Na$, —NH—$(CH_2)_n$—$SO_3K$, —NH—$(CH_2)_n$—$CO_2H$, —NH—$(CH_2)_n$—$CO_2Na$, or —NH—$(CH_2)_n$—$CO_2K$ (in which n is an integer between 1 and 3), or Formula 2:

Formula 2

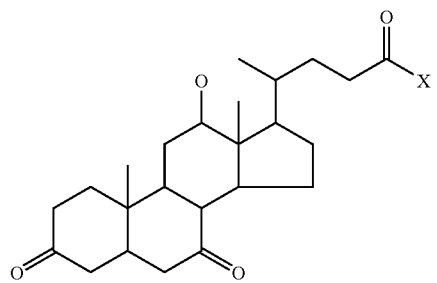

wherein X is as defined in Formula 1.

Cholic acid of the present invention has the chemical formula 3α,7α,12α-trihydroxycholan-24-oic acid, and is also termed ox bile extract, cholalic acid, cholalin or cholanic acid.

Examples of suitable cholic acid derivatives of the present invention include 3α,12α-dihydroxycholan-24-oic acid (deoxycholic acid), 3,7,12-trioxocholan-24-oic acid (dehydrocholic acid), 3α,7α-dihydroxycholan-24-oic acid (chenodeoxycholic acid), 3α,7β-dihydroxycholan-24-oic acid (ursodesoxycholic acid), 3α-hydroxycholan-24-oic acid (lithocholic acid), 2-[(3α,7α,12α-trihydroxy-24-oxocholan-24-yl)amino]ethanesulfonic acid (taurocholic acid), 2-(3α,7α,12α-trihydroxy-24-oxocholan-24-yl)glycine (glycocholic acid), and so on. Alkali metal salts and other derivatives that can be prepared from these cholic acid derivatives are also within the scope of the present invention. These cholic acid derivatives have a steroid structure as a common mother nucleus, and belong to steroid acids containing a carboxyl group. Acidic materials having a steroid mother nucleus which can be extracted from the bile of humans and animals, and salts with alkali metal ions thereof are also within the scope of the present invention.

Cholic acid and its derivatives produced in a living body are well known as main ingredients of bile secreted into the intestinal tract and reabsorbed in a volume of 500 mL daily. About 20 g to about 30 g of cholic acid and its derivatives, on a dry mass basis, are contained in the daily volume (500 mL) of the bile secreted into the upper part of the small intestine, among which about 0.5 g is discharged in the form of excrement in the course of intestinal re-absorption. About 400 mg is produced by the body each day to compensate for the loss. Accordingly, when the paroxetine cholate or cholic acid derivative salt of the present invention is administrated orally to treat depression in humans, the amount of cholic acid or its derivatives is limited to a maximum of 40 mg per day on a routine basis. Since the dose range of cholic acid or its derivatives by the paroxetine salt above, corresponds to about 0.13% to 0.2% of the total amount of circulating bile in human intestines, toxicity and side effects cannot be considered. Therefore, cholic acid and its derivatives are very suitable as salts of drugs. Particularly, cholic acid or ox bile extract is currently used as an emulsifier for foods in Japan, and is classified on the generally recognized as safe (GRAS) list by the FDA in the United States.

The paroxetine cholate or cholic acid derivative salt according to the present invention is in crystalline, non-crystalline or polycrystalline form. The crystalline or non-crystalline form is preferred. In the preparation of the paroxetine cholate or cholic acid derivative salt, the molar ratio of cholic acid or a derivative thereof to paroxetine in the form of free base is between 0.25:1 and 5:1, and preferably between 0.5:1 and 2:1.

The paroxetine cholate or cholic acid derivative salt according to the present invention can be prepared in accordance with the following procedure.

The paroxetine cholate or cholic acid derivative salt can be prepared by simply contacting the paroxetine free base with cholic acid or a derivative thereof in a given molar ratio. At this time, it is preferred that the free base is in a solution phase. More preferably, both the free base and the cholic acid or its derivative are in a solution phase. Specially, the paroxetine cholate or cholic acid derivative salt can be prepared by dissolving the paroxetine free base in an appropriate solvent and then, dissolving cholic acid or a derivative thereof in the solution; or by dissolving cholic acid or a derivative thereof in an appropriate solvent separately and then, mixing the obtained solution with a solution of the paroxetine free base previously dissolved.

The paroxetine used to prepare the salt may be in an oily free base form in which a salt portion is removed from a paroxetine salt, or a paroxetine salt itself. In the case where a paroxetine salt is used directly, it is advantageous in terms of effective separation and purification that a salt portion is volatile or highly soluble in solvents.

Suitable solvents used to prepare the salt are not specifically restricted so long as they can easily dissolve the free base. Also the solvents can be used to dissolve the cholic acid or its derivative. Examples of suitable solvents include water, and organic solvents, e.g., methanol, ethanol, n-propanol, isopropanol, n-butanol, isobutanol, dimethylsulfoxide, N,N-dimethylformamide, N,N-dimethylacetamide, methyl acetate, ethyl acetate, isopropyl acetate, acetone, methyl ethyl ketone, methyl isobutyl ketone, toluene, tetrahydrofuran, 1,4-dioxane, dimethoxyethane, dichloromethane, dichloroethane and ethyl ether. These solvents may be used alone or in combination of two or more solvents. The removal of the solvent used can be carried out by general processes, e.g., drying under reduced pressure or vacuum, volatilization, spray drying, lyophilization (freeze drying), cooling filtration, and combinations thereof, to prepare a solid crystalline, non-crystalline, or polycrystalline paroxetine cholate or cholic acid derivative salt. Drying under reduced pressure or vacuum, volatilization, and cooling filtration are preferably employed to prepare a crystalline paroxetine salt. Meanwhile, spray drying and lyophilization are preferably used to prepare a non-crystalline paroxetine salt.

To prepare the salt in a solid state in the presence of the solvent, first, paroxetine and the cholic acid or its derivative are dissolved in the single or mixed solvent. Thereafter, the obtained solution is allowed to stand under the temperature of 0° C., or another solvent is mixed with the solution to precipitate the paroxetine salt. The precipitate is filtered, washed with a cold solvent, and dried to afford the final paroxetine cholate or cholic acid derivative salt. The cold solvent used herein is selected from solvents which can be mixed with the single or mixed solvent but cannot readily dissolve the final paroxetine cholate or cholic acid derivative salt.

The paroxetine salt thus prepared may be obtained in anhydride or hydrate form. If the paroxetine salt is obtained in a solvate form, volatilization of intermolecular solvent is carried out in a dry oven or solvent displacement is carried out to remove the solvate.

For the purpose of improving the yield of the paroxetine cholate or cholic acid derivative salt, heating can be performed to increase the concentrations of the free base and the cholic acid or its derivative in the solution. Alternatively, the free base and the cholic acid or its derivative are dissolved in an appropriate solvent, and then a portion of the solvent can be removed by drying under vacuum or volatilization. Also, a crystal seed can be added to promote the precipitation of the paroxetine salt.

The present invention also provides a composition comprising paroxetine and cholic acid or a derivative thereof.

Although the paroxetine in free base or salt form is brought into contact with the cholic acid or its derivative in a specific molar ratio with or without water or an organic solvent, if complete or partial changes in the physical properties of the resulting salt, which reduce the taste or pain associated with paroxetine, are involved, those also fall within the scope of the present invention.

In the preparation of the composition according to the present invention, the molar ratio of the cholic acid or its derivative to the paroxetine free base is between 0.25:1 and 5:1, and preferably between 0.5:1 and 2:1. The composition of the present invention can be prepared by uniformly blending paroxetine and cholic acid or a derivative thereof in water or an organic solvent, followed by drying. The solvent used to prepare the composition of the present invention is identical to that used to prepare the paroxetine salt.

The present invention can provide a pharmaceutical composition comprising the paroxetine cholate or cholic acid derivative salt and a pharmaceutically acceptable excipient. The present invention also provides a pharmaceutical composition comprising paroxetine, cholic acid or a derivative thereof, and a pharmaceutically acceptable excipient. The pharmaceutical compositions of the present invention can be formulated into oral preparations for swallowing without water. A pharmaceutical composition comprising the paroxetine salt and the paroxetine composition (including paroxetine, cholic acid or a derivative thereof) is also within the scope of the present invention.

The pharmaceutically acceptable excipient can be at least one selected from diluents, binders, disintegrants, coloring agents, sweetening agents, flavors, preservatives, lubricants, and so on. Excipients having composite functions may be also used. Particularly, the pharmaceutically acceptable excipient can be at least one agent selected from excipients having natures of diluents and disintegrants and showing rapid disintegration properties, e.g., the products sold under the trade names Pharmaburst and Pharmagum. The diluent can be at least one selected from lactose, dextrose, microcrystalline cellulose, starch, and so on; the binder can be at least one selected from polyvinyl pyrrolidone, hydroxypropyl cellulose, hydroxypropylmethyl cellulose, hydroxyethyl cellulose, dicalcium phosphate, sodium alginate, and so on; the disintegrant can be at least one selected from sodium croscarmellose, sodium starch glycolate, crosslinked polyvinyl pyrrolidone, gelatinized starch, low-substituted hydroxypropyl cellulose, and so on; the coloring agent can be at least one selected from water-soluble colorants, tar colorants, and so on; the sweetening agent can be at least one selected from dextrose, sorbitol, mannitol, aspartame, acesulfame, citric acid, and so on; the flavor can be at least one selected from orange, grape, strawberry, blueberry flavor powders, and so on; the preservative can be at least one selected from benzoic acid, methyl paraben, ethyl paraben, propyl paraben, and so on; and the lubricant can be at least one selected from magnesium stearate, talc, hard anhydrous silica, sucrose fatty acid esters, and so on.

The pharmaceutical composition of the present invention can be formulated by conventional pharmaceutically approved techniques, e.g., blending, kneading, sieving, filling, and compressing.

The pharmaceutical composition of the present invention may be formulated into ordinary dosage forms, for example: solid oral preparations, such as tablets, capsules, granules, and powders; and liquid oral preparations, such as syrups; suppositories; and vial injections. Tablets, capsules and syrups for oral administration are preferred.

The pharmaceutical composition of the present invention may be administered by any convenient route, e.g., orally, sublingually, buccally, rectally, transdermally, parenterally, intravenously, intramuscularly, etc. Oral, sublingual, and buccal administrations are suitable for the object of the present invention because they allow the composition to be dissolved or swallowed in the mouth without water.

The pharmaceutical composition of the present invention can be administered for the treatment of depressive disorder in such an amount that the content of paroxetine is 20~50 mg/day; in such an amount that the content of paroxetine is 40 mg/day up to a maximum of 60 mg/day, initiating from 20 mg/day, for the treatment of obsessive-compulsive disorder; in such an amount that the content of paroxetine is 40 mg/day up to a maximum of 50 mg/day, initiating from 10 mg/day, for the treatment of panic disorder; in such an amount that the content of paroxetine is up to a maximum of 50 mg/day, initiating from 20 mg/day, if needed, increasing at a rate of 10 mg/day for the treatment of social phobia disorder and post-traumatic stress disorder; and in such an amount that the content of paroxetine is 20 mg/day for the treatment of generalized anxiety disorder.

BEST MODE FOR CARRYING OUT THE INVENTION

The constitutions and operations of the present invention will be explained in more detail with reference to the following examples. However, these examples are not to be construed as limiting the scope of the invention.

EXAMPLE 1

1.0 g of oily paroxetine free base and 1.24 g of cholic acid were completely dissolved in 20 mL of methanol while heating to 40° C. with shaking for 2 hours. The solvent was removed under reduced pressure, and then the residue was dried under vacuum, yielding 2.2 g of solid paroxetine cholate as a white powder.

EXAMPLE 2

1.0 g of oily paroxetine free base and 1.24 g of cholic acid were completely dissolved in a mixed solvent of methanol (10 mL) and acetone (40 mL) while heating to 40° C. with shaking for 30 minutes. The solution was allowed to stand at room temperature for 24 hours to obtain a salt. The salt was filtered, and dried under vacuum to yield 2.0 g of solid paroxetine cholate as a white crystal.

EXAMPLE 3

1.0 g of oily paroxetine free base and 1.24 g of cholic acid were completely dissolved in 10 mL of methanol while heating to 40° C. with shaking for one hour. The solution was slowly added dropwise to 100 mL of ethyl ether to precipitate a solid, stirred at 0° C. for 3 hours, and filtered. The filtered residue was washed with 30 mL of ethyl ether, and dried under vacuum to yield 1.89 g of solid paroxetine cholate as a light gray powder.

EXAMPLE 4

1.0 g of oily paroxetine free base and 1.24 g of cholic acid were completely dissolved in a mixed solvent of ethanol (20 mL) and isopropyl acetate (30 mL) while heating to 50° C. with shaking for 2 hours. The solution was allowed to stand at −20° C. for 48 hours, filtered, and dried under vacuum to yield 1.9 g of solid paroxetine cholate as a light gray powder.

EXAMPLE 5

1.0 g of oily paroxetine free base and 1.24 g of cholic acid were suspended in 50 mL of isopropanol. After the suspension was refluxed with stirring for 3 hours, it was slowly stirred at 25° C. for 2 hours, filtered and followed by drying under vacuum, yielding 2.15 g of solid paroxetine cholate as a white crystal.

EXAMPLE 6

1.0 g of oily paroxetine free base and 1.24 g of cholic acid were completely dissolved in a mixed solvent of purified water (5 mL) and methanol (30 mL) with stirring for 2 hours. The solution was allowed to stand at 0° C. for 48 hours, filtered, and dried under vacuum to yield 1.8 g of solid paroxetine cholate as a white powder.

EXAMPLE 7

1.0 g of oily paroxetine free base and 1.24 g of cholic acid were completely dissolved in a mixed solvent of ethanol (30 mL) and dichloromethane (50 mL) while heating to 50° C. with shaking for 3 hours. After the solution was distilled under reduced pressure to remove the dichloromethane, it was allowed to stand at 25° C. for 8 hours, filtered, and dried under vacuum to yield 1.94 g of solid paroxetine cholate as a white crystal.

EXAMPLE 8

1.0 g of oily paroxetine free base and 1.24 g of cholic acid were completely dissolved in 10 mL of N,N-dimethylformamide with stirring for 10 minutes. The solution was slowly added dropwise to 100 mL of isopropyl acetate to precipitate a solid, stirred at 0° C. for 3 hours, and filtered. The filtered residue was washed with 30 mL of ethyl ether, and dried under vacuum to yield 1.84 g of solid paroxetine cholate as a light gray powder.

EXAMPLE 9

1.0 g of oily paroxetine free base and 1.24 g of cholic acid were completely dissolved in 10 mL of N,N-dimethylacetamide while heating to 40° C. with shaking for 20 minutes. The solution was slowly added dropwise to 100 mL of ethyl ether to precipitate a solid, stirred at 0° C. for 3 hours, and filtered. The filtered residue was washed with 30 mL of ethyl ether, and dried under vacuum to yield 1.75 g of solid paroxetine cholate as a light gray powder.

EXAMPLE 10

1.0 g of oily paroxetine free base and 1.24 g of cholic acid were completely dissolved in 10 mL of dimethylsulfoxide with stirring for 5 minutes. The solution was slowly added dropwise to 100 mL of purified water to precipitate a solid, stirred at 0° C. for 3 hours, and filtered. The filtered residue was washed with 30 mL of ethyl ether, and dried under vacuum to give 1.7 g of solid paroxetine cholate as a white powder.

EXAMPLE 11

1.0 g of oily paroxetine free base and 1.19 g of deoxycholic acid were completely dissolved in 10 mL of methyl ethyl ketone while heating to 40° C. with shaking for one hour. The solution was left to stand at −20° C.~0° C. for 24 hours to precipitate a crystal, and filtered. The filtered residue was washed with cold methanol at 0° C. or below, and dried under vacuum to give 2.1 g of solid paroxetine deoxycholate as a white powder.

EXAMPLE 12

0.8 g of oily paroxetine free base and 1.13 g of glycocholic acid were completely dissolved in 20 mL of ethanol while heating to 40° C. with shaking for 3 hours. After the solution was concentrated under reduced pressure until about 5 mL of the solvent was left, it was allowed to stand at −20° C.~0° C. for 24 hours to precipitate a crystal, followed by filtration. The filtered residue was washed with cold methanol at 0° C. or less, and dried under vacuum to give 1.6 g of solid paroxetine glycocholate as a light gray powder.

EXAMPLE 13

0.8 g of oily paroxetine free base and 1.31 g of taurocholic acid were completely dissolved in a mixed solvent of purified water (5 mL) and ethanol (20 mL) while heating to 40° C. with shaking for one hour. After the solution was concentrated under reduced pressure until about 5 mL of the solvent was left, it was allowed to stand at −20° C.~0° C. for 24 hours to precipitate a crystal, followed by filtration. The filtered residue was washed with cold methanol at 0° C. or less, and dried under vacuum to give 1.8 g of solid paroxetine taurocholate as a light gray powder.

EXAMPLES 14–17

After paroxetine cholate, dicalcium phosphate, microcrystalline cellulose, and sodium croscarmellose were mixed together in compliance with the compositions of Examples 14 and 15 indicated in Table 1 below, each of the mixtures was passed through a 30 mesh standard sieve. Thereafter, magnesium stearate in the amounts shown in Table 1 was added to the respective sieved mixtures and further mixed, and the final mixture was compressed into tablets by common techniques.

Meanwhile, after paroxetine cholate, dicalcium phosphate, aspartame, and orange flavor powder were mixed together in compliance with the compositions of Examples 16 and 17 indicated in Table 1, each of the mixtures was passed through a 30 mesh standard sieve. Thereafter, Pharmagum S and magnesium stearate in the amounts shown in Table 1 were added to the respective sieved mixtures and further mixed, and the final mixture was compressed into tablets by common techniques. The tablets for oral administration could be taken or swallowed without water, leaving behind no bitter taste despite rapid disintegration in the mouth.

TABLE 1

Pharmaceutical compositions of Examples 14–17

|  | Example 14 | Example 15 | Example 16 | Example 17 |
|---|---|---|---|---|
| Paroxetine Cholate | 20.0 mg (as free base) | 30.0 mg (as free base) | 20.0 mg (as free base) | 30.0 mg (as free base) |
| Dicalcium Phosphate (DCPA) | 80.0 mg | 120.0 mg | 40.0 mg | 60.0 mg |
| Microcrystalline Cellulose | 50.0 mg | 75.0 mg | — | — |
| Sod. croscarmellose | 10.0 mg | 15.0 mg | — | — |
| Pharmagum S* | — | — | 240.0 mg | 360.0 mg |
| Aspartame | — | — | 0.2 mg | 0.3 mg |
| Orange Flavor Powder | — | — | 0.5 mg | 0.75 mg |
| Mg. Stearate | 1.5 mg | 2.25 mg | 1.5 mg | 2.25 mg |

*Pharmagum S: Trade name of rapidly disintegrating excipient commercially available from SPI Pharma.

EXAMPLES 18–21

After paroxetine glycocholate, microcrystalline cellulose, sodium croscarmellose, and L-hydroxypropyl cellulose were mixed together in compliance with the compositions of Examples 18 and 19 indicated in Table 2 below, each of the mixtures was passed through a 30 mesh standard sieve and kneaded with a binding solution prepared by dissolving Povidone K-30 in the amount shown in Table 2 in water. Each of the kneaded mixtures was dried in a dry oven at 40° C. until the loss of drying (LOD) was 2% or less, and passed through an 18 mesh standard sieve to obtain granular particles having a size of 18 mesh or less. Magnesium stearate in the amounts shown in Table 2 was added to the respective granular particles and further mixed, and the final mixture was compressed into tablets by common techniques.

Meanwhile, after paroxetine glycocholate and microcrystalline cellulose were mixed with each other in compliance with the compositions of Examples 20 and 21 indicated in Table 2, each of the mixtures was passed through a 30 mesh standard sieve and kneaded with a binding solution prepared by dissolving Povidone K-30 in water in the amount shown in Table 2.

Each of the kneaded mixtures was dried in a dry oven at 40° C. until the loss of drying (LOD) was 2% or less, and passed through a 24 mesh standard sieve to obtain granular particles having a size of 24 mesh or less. Pharmaburst X, grape flavor powder, citric acid powder having a size of 30 mesh or less, and magnesium stearate in the amounts shown in Table 2 was added to the respective granular particles and further mixed, and the final mixture was compressed into tablets by common techniques. The tablets for oral administration could be taken or swallowed without water, leaving behind no bitter taste despite rapid disintegration in the mouth.

TABLE 2

Pharmaceutical compositions of Examples 18–21

|  | Example 18 | Example 19 | Example 20 | Example 21 |
|---|---|---|---|---|
| Paroxetine Glycocholate | 20.0 mg (as free base) | 30.0 mg (as free base) | 20.0 mg (as free base) | 30.0 mg (as free base) |
| Povidone K-30 | 10.0 mg | 15.0 mg | 15.0 mg | 22.5 mg |
| Microcrystalline Cellulose | 100.0 mg | 150.0 mg | 100.0 mg | 150.0 mg |
| Sod. Croscarmellose | 10.0 mg | 15.0 mg | — | — |
| L-Hydroxypropyl Cellulose | 30.0 mg | 40.0 mg | — | — |
| Pharmaburst X* | — | — | 240.0 mg | 320.0 mg |
| Grape Flavor Powder | — | — | 1.0 mg | 1.5 mg |
| Citric Acid | — | — | 1.0 mg | 1.5 mg |
| Mg. Stearate | 1.5 mg | 2.25 mg | 1.5 mg | 2.25 mg |

*Pharmaburst X: Trade name of rapidly disintegrating excipient commercially available from SPI Pharma.

EXAMPLES 22–25

After paroxetine taurocholate, microcrystalline cellulose, sodium croscarmellose, and L-hydroxypropyl cellulose were mixed together in compliance with the compositions of Examples 22 and 23 indicated in Table 3 below, each of the mixtures was passed through a 30 mesh standard sieve and kneaded with a binding solution prepared by dissolving Povidone K-30 in water in the amount shown in Table 3. Each of the kneaded mixtures was dried in a dry oven at 40° C. until the loss of drying (LOD) was 2% or less, and passed through an 18 mesh standard sieve to obtain granular particles having a size of 18 mesh or less. Magnesium stearate in the amounts shown in Table 3 was added to the respective granular particles and further mixed, and the final mixture was compressed into tablets by common techniques.

Meanwhile, after paroxetine taurocholate and microcrystalline cellulose were mixed with each other in compliance with the compositions of Examples 24 and 25 indicated in Table 3, each of the mixtures was passed through a 30 mesh standard sieve and kneaded with a binding solution prepared by dissolving Povidone K-30 in water in the amount shown in Table 3.

Each of the kneaded mixtures was dried in a dry oven at 40° C. until the loss of drying (LOD) was 2% or less, and passed through a 24 mesh standard sieve to obtain granular particles having a size of 24 mesh or less. Pharmaburst X, grape flavor powder, citric acid powder having a size of 30 mesh or less, and magnesium stearate in the amounts shown in Table 3 were added to the respective granular particles and further mixed, and the final mixture was compressed into tablets by common techniques. The tablets for oral administration could be taken or swallowed without water, leaving behind no bitter taste despite rapid disintegration in the mouth.

TABLE 3

Pharmaceutical compositions of Examples 22–25

| | Example 22 | Example 23 | Example 24 | Example 25 |
|---|---|---|---|---|
| Paroxetine Taurocholate | 20.0 mg (as free base) | 30.0 mg (as free base) | 20.0 mg (as free base) | 30.0 mg (as free base) |
| Povidone K-30 | 10.0 mg | 15.0 mg | 16.0 mg | 23.0 mg |
| Microcrystalline Cellulose | 90.0 mg | 130.0 mg | 110.0 mg | 150.0 mg |
| Sod. Croscarmellose | 15.0 mg | 20.0 mg | — | — |
| L-Hydroxypropyl Cellulose | 30.0 mg | 40.0 mg | — | — |
| Pharmaburst X* | — | — | 260.0 mg | 340.0 mg |
| Grape Flavor Powder | — | — | 2.0 mg | 2.5 mg |
| Citric Acid | — | — | 1.0 mg | 1.5 mg |
| Mg. Stearate | 1.5 mg | 2.25 mg | 1.5 mg | 2.25 mg |

*Pharmaburst X: Trade name of rapidly disintegrating excipient commercially available from SPI Pharma.

EXAMPLES 26 AND 27

After paroxetine cholate, dicalcium phosphate, microcrystalline cellulose, and sodium croscarmellose were mixed together in compliance with the compositions of Examples 14 and 15 indicated in Table 1 above, each of the mixtures was passed through a 30 mesh standard sieve for examples 26 and 27, respectively. Thereafter, magnesium stearate in the amounts shown in Table 1 was added to the respective sieved mixtures and further mixed, and the final mixture was filled into a #2 capsule by common techniques.

EXAMPLES 28 AND 29

After paroxetine glycocholate, microcrystalline cellulose, sodium croscarmellose, and L-hydroxypropyl cellulose were mixed together in compliance with the compositions of Examples 18 and 19 indicated in Table 2 above, each of the mixtures was passed through a 30 mesh standard sieve and kneaded with a binding solution prepared by dissolving Povidone K-30 in water in the amount shown in Table 2 above, for Examples 28 and 29, respectively. Each of the kneaded mixtures was dried in a dry oven at 40° C. until the loss of drying (LOD) was 2% or less, and passed through an 18 mesh standard sieve to obtain granular particles having a size of 18 mesh or less. Magnesium stearate in the amounts shown in Table 2 was added to the respective granular particles and further mixed, and the final mixture was filled into a #2 capsule by common techniques.

EXAMPLES 30 AND 31

Each 1.51 g and 3.02 g of paroxetine hydrochloride salt was homogeneously mixed with 1.65 g of cholic acid, and then kneaded with each 0.7 g and 1 g_of a binding solution prepared by dissolving Povidone K-30 in ethanol in the amount of 30 w/v %, for Examples 30 and 31, respectively. The kneaded mixture was dried in a dry oven at 40° C. until the loss of drying (LOD) was 2% or less, and passed through a 30 mesh standard sieve to obtain granular particles having a size of 30 mesh or less. The final granular particle was used as paroxetine compositions containing cholic acid.

EXAMPLES 32 AND 33

After each amount corresponding to 20 mg of the paroxetine free base was sampled from the respective paroxetine compositions prepared in Examples 30 and 31, each of the samples was mixed with dicalcium phosphate, microcrystalline cellulose and sodium croscarmellose in compliance with the composition of Example 14 indicated in Table 1 above and filtered through a 30 mesh standard sieve for Examples 32 and 33, respectively. Magnesium stearate in the amounts shown in Example 14 was added to the respective sieved mixtures and further mixed, and the final mixture was compressed into tablets by common techniques.

EXAMPLE 34

0.5 g of ethanol was added to 1.33 g of paroxetine free base to obtain a slurry, and then 3.3 g of cholic acid was added thereto. The resulting mixture was kneaded, dried in a dry oven at 40° C. until the loss of drying (LOD) was 2% or less, and passed through a 30 mesh standard sieve to obtain granular particles having a size of 30 mesh or less, which was used as a paroxetine composition containing cholic acid.

EXAMPLE 35

After the amount corresponding to 20 mg of paroxetine free base was sampled from the paroxetine composition prepared in Example 34, the sample was mixed with dicalcium phosphate, aspartame, and orange flavor powder in compliance with the composition of Example 16 indicated in Table 1 above, and filtered through a 30 mesh standard sieve. Pharmagum S and magnesium stearate in the amounts shown in Example 16 were added to the sieved mixture and further mixed, and the final mixture was compressed into tablets by common techniques. The tablets for oral administration could be eaten and swallowed without water, leaving behind no bitter taste despite rapid disintegration in the mouth.

COMPARATIVE EXAMPLE 1

Taste Comparison

After 5 mg of drug in solid state from each of the drugs shown in Table 4 was sampled without using any excipient, water or other solvents, the taste of the drugs was evaluated by three panelists over a period of 10 minutes in the mouth. Paroxetine initially leaves a characteristic bitter taste even in small amounts, and then causes irritating pain along with an intolerable bitter taste with the passage of time.

According to the experimental results (Table 4), other paroxetine salts except paroxetine cholate and paroxetine glycocholate initially left a bitter taste and caused irritating pain along with a bitter taste with the passage of time. Particularly, currently marketed or approved paroxetine hydrochloride and paroxetine methanesulfonate left a bitter taste inherent in paroxetine and incurred a strong rejection by the panelists. In contrast, the paroxetine cholate and paroxetine glycocholate of the present invention removed the bitter taste and pain inherent in paroxetine and incurred no rejection by the panelists. In addition, it was confirmed that reduction of the characteristic taste and pain of paroxetine could also be achieved by only blending paroxetine with cholic acid. Accordingly, the paroxetine cholate or cholic acid derivative salt and the composition comprising paroxetine and cholic acid or derivative thereof of the present invention are suitable as orally disintegrating tablets for anti-depressants.

TABLE 4

|  | Initial taste (within one min.) | Later taste (after one min.) |
|---|---|---|
| Paroxetine cholate | No taste | No pain |
| Mixture of paroxetine and cholic acid (1:1, molar ratio) | Slightly bitter taste | No pain |
| Paroxetine glycocholate | No taste | No pain |
| Paroxetine glucuronate | Bitter taste | Irritating pain caused |
| Paroxetine HCl | Very bitter taste | Irritating pain caused |
| Paroxetine methanesulfonate | Very bitter taste | Irritating pain caused |
| Paroxetine tartarate | Very bitter taste | Irritating pain caused |
| Paroxetine napsylate | Very bitter taste | Irritating pain caused |

COMPARATIVE EXAMPLE 2

Stability Comparison

Each of the drugs shown in Table 5 was completely dissolved in a 0.3% hydrogen peroxide solution at a concentration of 1 mg/mL. While storage under stressed conditions at 80° C., changes in the contents of the drugs were monitored. The 0.3% hydrogen peroxide solution is a solution commonly used to quickly determine the stability of drugs and provides stressed conditions for artificial acceleration of the oxidation of the drugs. The content analysis was conducted by HPLC in accordance with the paroxetine content analysis defined in USP.

HPLC analysis indicated that paroxetine cholate and paroxetine glycocholate are highly stable when compared to other paroxetine salts. Particularly, the contents of currently marketed or approved paroxetine hydrochloride and paroxetine methanesulfonate rapidly decreased to 54% or below for 48 hours, and to about 15% or below within 120 hours after storage. The results indicate that such drugs cause nearly complete loss of the drugs within 120 hours. In contrast, the salts of the present invention were maintained at a content level of 89% or more for 48 hours and 54% or more for 120 hours after storage. Accordingly, the salts of the present invention turned out to be surprisingly stable. In addition, it was confirmed that the improvement in stability could also be achieved by only blending paroxetine with cholic acid.

TABLE 5

Stability comparison of paroxetine salts under severe conditions (chamber at 80° C., 0.3% hydrogen peroxide)

|  | Initial | 24 hrs | 48 hrs | 72 hrs | 120 hrs | 144 hrs |
|---|---|---|---|---|---|---|
| Paroxetine cholate | 100.0% | 98.2% | 92.4% | — | 66.3% | — |
| Mixture of paroxetine and cholic acid (1:1, molar ratio) | 100.0% | 97.4% | 90.3% | — | 63.9% | — |
| Paroxetine glycocholate | 100.0% | 96.8% | 89.6% | — | 54.3% | — |
| Paroxetine glucuronate | 100.0% | 92.8% | 59.0% | — | 12.3% | — |
| Paroxetine HCl | 100.0% | 84.5% | 53.8% | — | 13.4% | — |
| Paroxetine methanesulfonate | 100.0% | 74.4% | 31.8% | 16.6% | — | — |
| Paroxetine tartarate | 100.0% | 81.3% | — | 28.3% | — | 4.8% |
| Paroxetine napsylate | 100.0% | 60.4% | — | 16.1% | — | 3.5% |

INDUSTRIAL APPLICABILITY

As apparent from the above description, in the novel paroxetine salts and paroxetine composition of the present invention, the bitter taste inherent in paroxetine is completely removed not by a way hiding the bitter taste with complexes using ion-exchange resins, clathrates using cyclodextrins, coatings using polymers, other material having an intense flavor and taste, and so on, like conventional techniques, but by a way forming paroxetine salt with cholic acid or its derivatives having a slightly bitter taste. That is, this way of the present invention is to completely remove the taste of paroxetine itself without modification of the taste. Thus it surprisingly eliminates the characteristic taste and pain associated with paroxetine.

In addition, unlike the glycyrrhyzinic acid and glycyrrhyzinate salts disclosed in PCT Publications WO 03/013470 and WO 03/013529 in which the intense flavor and taste of liquorice induce changes in the taste of paroxetine, the salts of the present invention uses cholic acid or its derivatives having a slightly bitter taste to completely remove the bitter taste inherent in paroxetine without any taste changes.

Furthermore, the paroxetine cholate and paroxetine cholic acid derivative salts of the present invention have excellent stability against oxidation, which is considered to be a main factor decreasing the content of drugs in the evaluation of drug stability, as compared to other paroxetine salts.

Therefore, the paroxetine cholate and paroxetine cholic acid derivative salts of the present invention are suitable as agents for oral administration swallowing it without water, particularly solid anti-depressants, and can be applied to liquid preparations due to their excellent stability.

Moreover, no taste and superior stability of paroxetine can be achieved not only through the formation of the paroxetine salt but also through blending of paroxetine with cholic acid or a derivative thereof.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A paroxetine cholate or cholic acid derivative salt thereof, wherein the cholic acid and its derivative are represented by Formula 1:

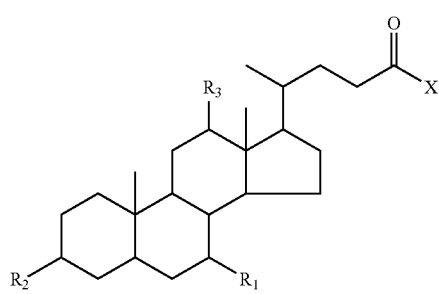

wherein $R_1$, $R_2$, and $R_3$ are independently hydrogen or a hydroxy group; and X is —OH, —ONa, —NH—$(CH_2)_n$—$SO_3H$, —NH—$(CH_2)_n$—$SO_3Na$, —NH—$(CH_2)_n$—$SO_3K$, —NH—$(CH_2)_n$—$CO_2H$, —NH—$(CH_2)_n$—$CO_2Na$, or —NH—$(CH_2)_n$—$CO_2K$ (in which n is an integer between 1 and 3),
or Formula 2:

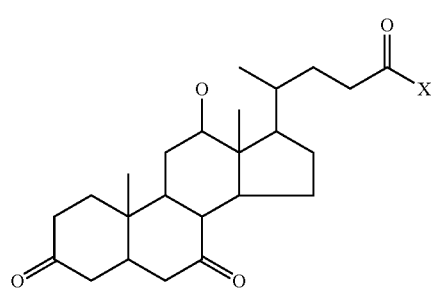

wherein X is as defined in Formula 1.

2. The salt according to claim 1, wherein the salt is a paroxetine cholate salt.

3. The salt according to claim 1 or 2, wherein the paroxetine salt is in crystalline form.

4. The salt according to claim 1 or 2, wherein the paroxetine salt is in non-crystalline form.

5. A pharmaceutical composition comprising the paroxetine salt according to claim 1 or 2 and a pharmaceutically acceptable excipient.

6. The composition according to claim 5, wherein the composition is formulated into an oral preparation for swallowing without water.

7. A composition comprising paroxetine and cholic acid or a derivative thereof, wherein the cholic acid and its derivative are represented by Formula 1:

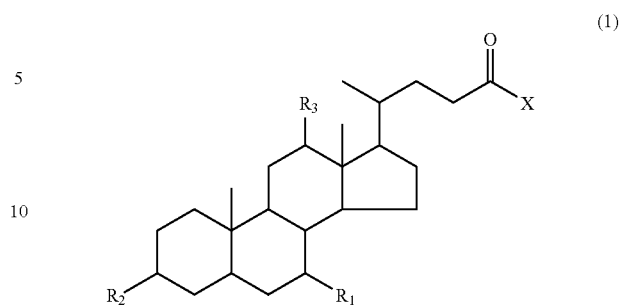

wherein $R_1$, $R_2$, and $R_3$ are independently hydrogen or a hydroxy group; and X is —OH, —ONa, —NH—$(CH_2)_n$—$SO_3H$, —NH—$(CH_2)_n$—$SO_3Na$, —NH—$(CH_2)_n$—$SO_3K$, —NH—$(CH_2)_n$—$CO_2H$, —NH—$(CH_2)_n$—$CO_2Na$, or —NH—$(CH_2)_n$—$CO_2K$ (in which n is an integer between 1 and 3),
or Formula 2:

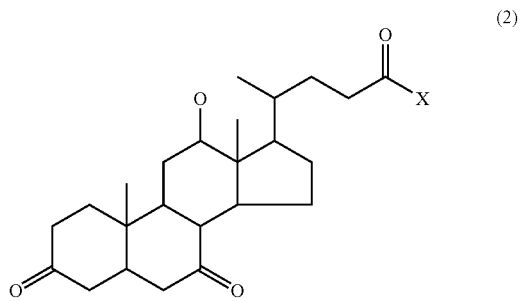

wherein X is as defined in Formula 1.

8. The composition according to claim 7, wherein the molar ratio of the cholic acid or its derivative to the paroxetine is between 0.5:1 and 2:1.

9. The composition according to claim 7 or 8, wherein the composition is prepared by uniformly blending paroxetine and cholic acid or a derivative thereof in water or an organic solvent, followed by drying.

10. A pharmaceutical composition comprising the composition according to claim 7 or 8 and a pharmaceutically acceptable excipient.

11. The pharmaceutical composition according to claim 9, further comprising a pharmaceutically acceptable excipient.

12. The pharmaceutical composition according to claim 10, wherein the composition is formulated into an oral preparation for swallowing without water.

13. The pharmaceutical composition according to claim 11, wherein the composition is formulated into an oral preparation for swallowing without water.

14. A method for treating depressive disorder, comprising administering a therapeutically effective amount of the paroxetine cholate or cholic acid derivative salt according to claim 1 to a human in need of such treatment.

15. A method for treating depressive disorder, comprising administering a therapeutically effective amount of the composition according to claim 7 to a human in need of such treatment.

* * * * *